United States Patent [19]

Kim et al.

[11] 4,440,934
[45] Apr. 3, 1984

[54] 5-(4-HYDROXYPHENYL) HYDANTOIN DERIVATIVES

[75] Inventors: Sung J. Kim; Ik W. Um, both of Seoul; Won J. Park, Anyang, all of Rep. of Korea

[73] Assignee: Pacific Chemical Ind. Co., Ltd., Seoul, Rep. of Korea

[21] Appl. No.: 411,783

[22] Filed: Aug. 26, 1982

[30] Foreign Application Priority Data

Aug. 26, 1981 [KR] Rep. of Korea ........................ 81-3119
Apr. 30, 1982 [KR] Rep. of Korea ........................ 82-1902

[51] Int. Cl.³ .............................................. C07D 233/78
[52] U.S. Cl. ...................................... 548/312; 548/314
[58] Field of Search ........................................ 548/312

[56] References Cited

U.S. PATENT DOCUMENTS 3,987,184 10/1976 Foelsch ........................... 548/312 X

FOREIGN PATENT DOCUMENTS 1319 4/1979 European Pat. Off. ............ 548/314

OTHER PUBLICATIONS

March, J., *Advanced Organic Chemistry*, McGraw Hill, New York, 1968, pp. 403-404.
Chemical Abstracts 58: 6921g (1963) [Kawahara et al., *Yakugaku Zasshi*, 82, 912-915 (1962)].

*Primary Examiner*—Richard A. Schwartz
*Attorney, Agent, or Firm*—Sughrue, Mion, Zinn, Macpeak & Seas

[57] ABSTRACT

Compounds of the formula (I)

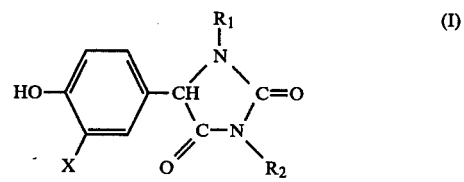

wherein
$R_1$ represents a hydrogen atom or a 1-hydroxy lower alkyl radical and the like;
$R_2$ represents a 1-hydroxy lower alkyl radical; and
X represents a hydrogen or chlorine atom
having broad spectrum antimicrobial activity and a process for their production.

4 Claims, No Drawings

5-(4-HYDROXYPHENYL) HYDANTOIN DERIVATIVES

DETAILED DESCRIPTION OF THE INVENTION

The present invention relates to novel compounds of the below mentioned general formula (I) which possess a strong and broad spectrum antimicrobial activity, and to a process for its manufacture.

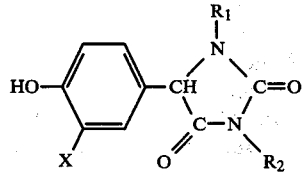
(I)

In the formula stated above $R_1$ represents a hydrogen atom or a 1-hydroxy lower alkyl radical and the like and $R_2$ represents a 1-hydroxy lower alkyl radical, and X represents a hydrogen or chlorine atom.

As used in this specification, the term "lower alkyl" means such a alkyl radical which contains from 1 to 3 carbon atoms as methyl, ethyl, propyl and the like.

A preferred group of the compounds out of the above mentioned formula(I) is those where X and $R_1$ are a hydrogen atom, $R_2$ is a hydroxymethyl radical or X is a hydrogen atom, $R_1$ and $R_2$ are a hydroxymethyl radical or X is a hydrogen atom, $R_1$ and $R_2$ are a 1-hydroxyethyl radical or X is a hydrogen atom, $R_1$ and $R_2$ are a 1-hydroxypropyl radical, or X is a chlorine atom, $R_1$ is a hydrogen atom and $R_2$ is a hydroxymethyl radical.

Examples of compounds of formula I hereinbefore are:

5-(4-hydroxyphenyl)-3-hydroxymethylhydantoin (compound A)

5-(4-hydroxyphenyl)-1,3-bis (hydroxymethyl)hydantoin (compound B)

5-(4-hydroxyphenyl)-1,3-bis (1-hydroxyethyl)hydantoin (compound C)

5-(4-hydroxyphenyl)-1,3-bis (1-hydroxypropyl)hydantoin (compound D) and 5-(3-Chloro-4-hydroxyphenyl)-3-hydroxymethylhydantoin (compound E).

The detailed manufacturing process of the compounds provided by the present invention are as follows:

5-(4-hydroxyphenyl)hydantoin of the formula(II) is reacted with aldehyde of the formula(III) at a temperature of from 40° C. to 80° C. for from 3 to 5 hours in a solvent of water, alcohol, or aqueous alcohol after arranging at a pH of 5 to 8.5. The formula ($I_a$) or ($I_b$) is obtained then.

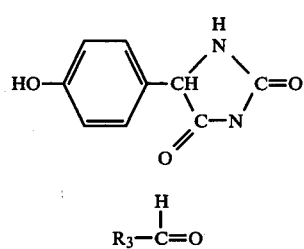

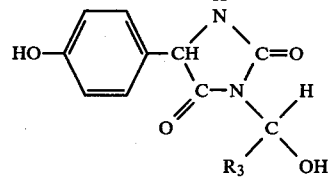
(Ia)

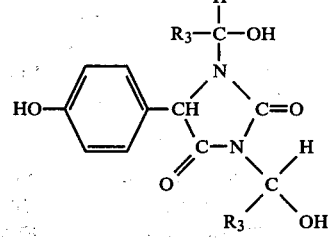
(Ib)

In the formulae stated above $R_3$ represents a hydrogen atom, methyl or ethyl radical.

The above mentioned formula(III) aldehyde represents formaldehyde, acetaldehyde, or propionaldehyde, and 5-(3-chloro-4-hydroxyphenyl)-3-hydroxymethylhydantoin is manufactured as follows:

5-(4-hydroxyphenyl)hydantoin of the formula(II) is dissolved in methanol and chlorine gas is subsequently passed into the solution at a temperature of from 25° C. to 35° C. for from 1 to 2 hours. After then the solvent is recollected under reduced pressure and the distilled water is added in order to precipitate 5-(3-Chloro-4-hydroxyphenyl)hydantoin of the formula(IV) stated below.

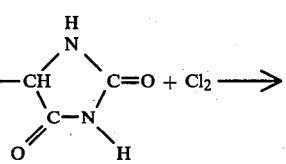
(II)

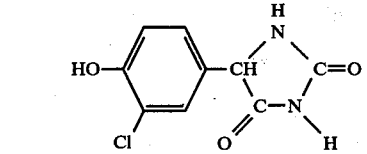
(IV)

5-(3-Chloro-4-hydroxyphenyl)hydantoin so obtained is then dispersed into distilled water or dissolved in methanol. After adding formaldehyde 35% and adjusting the PH of the solution to PH 7 to 7.5 by adding 0.1 aqueous ammonia, the reaction is carried out at a temperature range of from 60° C. to 80° C. for 4 to 6 hours. Then the 5-(3-Chloro-4-hydroxyphenyl)-3-hydroxymethylhydantoin of the formula($I_c$) is produced.

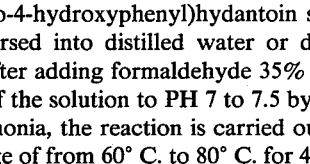
(Ic)

-continued

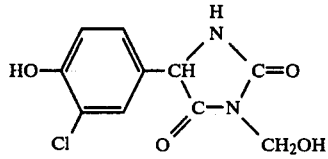

With regard to the process of preparing the novel compounds provided by the present invention, the reaction temperature and the PH of the reaction mixture are the factors which play an important role in the point of the reaction speed and yield of the reaction product. In other words, when the reaction temperature is highly increased in order to speed up the reaction, the yield of the reaction product is decreased due to the unfavorable decrease of the aldehyde or such a negative reaction as an occurrence of condensed products. In addition, if the PH of the reaction mixture is raised the speed of the reaction is rapidly increased. It, however, causes a lowering of the yield owing to the negative reactions of not only an opening of hydantoin ring but also an autooxidative and reductive reaction of formaldehyde in part by alkali. In this connection, when the said negative reactions are inhibited by reducing the pH of the reaction mixture, the speed of the reaction becomes very slow due to lower boiling point and weak reactivity of acetaldehyde, proionaldehyde and the like and the material is produced which is sparingly soluble and presumed an intermolecular removal reactant. According to the present inventions' study it is invented that the proper reaction speed can be maintained and in addition the said negative reactions inhibited when the reaction is carried out in a solvent of water, alcohol, or aqua alcohol and at a temperature of 40° C. to 80° C. with keeping the pH of the reaction solution at a pH of 5 to 8.5 in accordance with the reaction easiness.

The final active compounds according to the invention are especially useful because they are active against many micro-organisms, including bacteria, yeast and molds.

In other words, the compounds are not just active against one or a few organisms, rather they display broad spectrum antimicrobial activity.

Compared to the previously known antimicrobial agents, the compounds shown almost equal or even superior to those of widely used antimicrobial agents.

In order to assay the effectiveness of the compounds of the present invention, the MIC(minimum inhibitory concentration) on bacteria, yeast and fungi were determined.

The following micro-organisms were used for the experiments.

(1) bacteria (1-1)

Grame Positive
*Bacillus subtilis*
*Staphylococus aureus*

(1-2)

Gram negative
*Pseudomomas aeruginosa*
*Escherichia coli*
(2) Yeast
*Candida albicans*
(3) Mold

*Aspergillus niger*
*Aspergillus flavus*
*Tricoderma virid*
*Fusarium solani*

Minimum inhibitory concentrations were determined according to following procedure.

For the bacteriostatic activity, the said invention compounds were serially diluted with 10 ml of sterile nutrient broth. Each tube was inoculated with 1 drop of an aqueous suspension of the various test organisms containing approximately $1 \times 10^6$ organisms/ml and incubated at 37 C. for 48 hrs. After incubation, the IMC of the said invention compounds were determined as the lowest concentration of compound in which no microscopic evidence of growth was observed. The compounds and the MIC value against bacteria of the compounds can be seen from the following table 1.

TABLE 1

| | The MIC value against bacteria of the compounds according to the present invention. % (W/V) | | | |
|---|---|---|---|---|
| Compound | *Pseudomonas aeruginosa* | *Escherichia coli* | *Staphylococcus aureus* | *Bacillus subtilis* |
| A | 0.02 | 0.01 | 0.02 | 0.03 |
| B | 0.01 | 0.01 | 0.01 | 0.02 |
| C | 0.12 | 0.07 | 0.07 | 0.1 |
| D | 0.15 | 0.09 | 0.1 | 0.12 |
| E | 0.01 | 0.01 | 0.01 | 0.05 |

As seen in the table 1, the compound A has the MIC value of 0.01–0.03% which is similar to the 0.01–0.02% of the compound B 0.01–0.05% of the compound E but is about 10 times as strong as the compound C and D of 0.07–0.15%.

For the evaluation of fungistatic activity, each compound was serially diluted in test tubes to give the desired concentration when mixed with 20 ml of steriled molten sabouraud dextrose agar, and poured into sterile petri dishes.

After the medium was solidified, the spore-suspension of the each test organisms were inoculated by streaking and incubated at 25 C. for 7 days.

The minimum concentration of the compound effective for inhibiting the growth is determined by examining the growth of the each organism.

In the above mentioned method the MIC for yeast and molds of the compounds A,B,C,D and E were obtained and can be seen from the table 2.

TABLE 2

| | The MIC for molds and yeast of the compounds of the present invention. % (W/V) | | | | |
|---|---|---|---|---|---|
| Compound | *Aspergillus niger* | *Aspergillus flavus* | *Tricoderma virid* | *Fusarium solani* | *Candida albicans* |
| A | 0.2 | 0.3 | 0.1 | 0.15 | 0.4 |
| B | 0.1 | 0.2 | 0.1 | 0.1 | 0.2 |
| C | 0.4 | 0.5 | 0.3 | 0.3 | 0.5 |
| D | 0.3 | 0.5 | 0.2 | 0.3 | 0.5 |
| E | 0.2 | 0.2 | 0.1 | 0.1 | 0.2 |

As seen in table 2 the compound A,B and E showed stronger fungistatic activities than the compounds C and D. It, however, can be seen from the comparison with the table 1 that all the compounds A,B,C,D and E exhibit by far stronger activities against bacteria than fungi and yeast.

EXAMPLE 1

5-(4-hydroxyphenyl)hydantoin (10.2 g) dispersed into distilled water (50 g) was added with paraformaldehyde (purity 85%, 3.53 g). The reaction mixture was then adjusted to about pH 6 by adding acetic acid and stirred for 4 hours. As the reaction was in progress, all the reaction mixture became gradually transparent due to high solubility of the reaction product.

When the reaction mixture was dissolved completely and homogeneously—which is considered as a reaction—completed point—the solvent was distilled under the reduced pressure and then the viscous oily liquid was remained. After the homogeneous solution was made by adding acetone (50 ml), the precipitate produced at a cooling place with adding benzene dropwise was filtered and dried:

It was identified from the values of infra-red spectrophotometer, nuclear magnetic resonance spectrum and atom analysis that the chemical structure of this white crystal is 5-(4-hydroxyphenyl)-3-hydroxymethylhydantoin.

yield: 84.3%.
m.p.: 142°–144° C.

|  | Analysis of Atom | | | |
|---|---|---|---|---|
|  | C % | H % | N % | O % |
| Required | 54.05 | 4.50 | 12.61 | 28.82 |
| Found | 54.01 | 4.58 | 12.48 | 28.92 |

EXAMPLE 2

The 5-(4-hydroxyphenyl)hydantoin (19.2 g) dispersed into distilled water (50 g) was added with formaldehyde (85%, 7.06 g). The reaction solution adjusted to a pH of 7 by adding 0.1 N ammonium hydroxide solution was heated slowly up to 80° C. and then stirred for 4 hours. Concentration was carried out under reduced pressure until the reaction solution became the viscous oily liquid. After crystallisation was made from this oily liquid with using acetone and benzene, and it was filtered and dried. There was obtained the hygroscopic white crystals 19.9 g.

It was identified from the values of infra-red spectrophotometer and nuclear magnetic resonance spectrum that the chemical structure of this white crystal is 5-(4-hydroxyphenyl)-1,3-bis(hydroxymethyl)hydantoin.

yield: 79.1%.

EXAMPLE 3

The 5-(4-hydroxyphenyl)hydantoin (19.2 g) dispersed into ethanol (50 ml) was added with acetaldehyde (15 g). The reaction mixture was adjusted to a pH of 8 by adding 0.1 N ammonium hydroxide and then a reflux was carried out for 4 hours. After confirming by a thin chromatography method that the reaction was completed, the excessively remained acetaldehyde and solvent were concentrated. The white crystals obtained thereof were recrystallized with using methanol (50%). There is obtained the white needle-shaped crystals 22.8 g.

It was identified from the values of infra-red spectrophotometer and nuclear magnetic resonance spectrum that the chemical structure of this white crystal is 5-(4-hydroxyphenyl)-1,3-bis(1-hydroxyethyl)hydantoin.

yield: 81.5%.
m.p.: 287° C.

EXAMPLE 4

The 5-(4-hydroxyphenyl)hydantoin (19.2 g) dispersed with into ethanol (50 ml) was added with propoinaldehyde (15 g). After the reaction mixture was adjusted to a pH of 8 by adding 0.1 N ammonium hydroxide, the process was carried out in the same manner as Example 3. Recrystallisation from 80% methanol gave the white needle-shaped crystals (23.9 g).

It was identified from the values of infra-red spectrophotometer and nuclear magnetic reasonance spectrum that the chemical structure of this material is 5-(4-hydroxyphenyl)-1,3-bis(1-hydroxypropyl)hydantoin.

yield: 77.5%.
m.p.: 282°–284° C.

EXAMPLE 5

(a) Chlorine gas obtained by adding slowly conc-HCl (53 g) into potassium permanganate (15 g) was washed with water and dried with sulfuric acid. This gas was then poured into a solution of 5-(4-hydroxyphenyl)-hydantoin (30 g) dissolved in methanol (500 ml) and thereafter the reaction solution was stirred vigorously. While chlorine gas was produced and reacted for 2 hours, the reaction temperature was maintained at 30° C. Thereafter the temperature of the reaction mixture was raised slowly up to about 50° C., at which stirring was made for 30 minutes. Then the solvent was recollected under reduced pressure and the white precipitate obtained by adding distilled water (200 ml) was filtered and washed twice with water. Recrystallisation from 50% methanol gave the white needle-shaped crystals (30.8 g). It was identified from the values of infra-red spectrophotometer and nuclear magnetic resonance spectrum that the structure of this material is 5-(3-chloro-4-hydroxyphenyl)hydantoin.

m.p.: 238°–240° C.

(b) The 5-(3-chloro-4-hydroxyphenyl)hydantoin (10 g) dispersed into distilled water (100 ml) was added with 35% formaldehyde solution (3.8 g). After the reaction solution was arranged at a pH of 7.3 by adding 0.1 N aqueous ammonia, the temperature was slowly raised up to 70°–80° C. and the reaction was carried out with stirring for 4 hours. The solvent was distilled under reduced pressure, from which recrystallisation gave the white needle-shaped crystal (9.1 g).

It was identified from the values of infra-red spectrophotometer and nuclear magnetic resonance spectrum that the structure of this white needle-shaped crystal is 5-(3-chloro-4-hydroxyphenyl)-3-hydroxymethylhydantoin.

yield: 81%.
m.p.: 197°–199° C.

What is claimed is:

1. A 5-(4-hydroxyphenyl)hydantoin derivative of the formula(I)

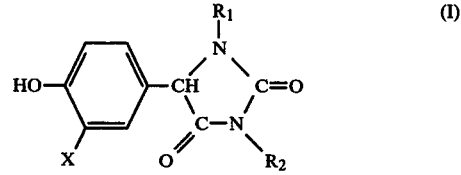

wherein $R_1$ represents a hydrogen atom or a 1-hydroxy lower alkyl radical, and $R_2$ represents a 1-hydroxy lower alkyl radical, and X represents a hydrogen or chlorine atom.

2. The compound of claim 1 wherein $R_1$ is hydrogen or 1-hydroxymethyl, and $R_2$ is 1-hydroxymethyl, and X is hydrogen or chlorine.

3. The compound of claim 1 wherein $R_1$ is hydrogen or 1-hydroxyethyl, and $R_2$ is 1-hydroxyethyl, and X is hydrogen.

4. The compound of claim 1 wherein $R_1$ is 1-hydroxypropyl, and $R_2$ is 1-hydroxypropyl, and X is hydrogen.

* * * * *